United States Patent [19]
Domankevitz et al.

[11] Patent Number: 6,126,655
[45] Date of Patent: Oct. 3, 2000

[54] APPARATUS AND METHOD FOR SELECTIVE LASER-INDUCED HEATING OF BIOLOGICAL TISSUE

[75] Inventors: Yacov Domankevitz, Brookline; R. Rox Anderson, Lexington, both of Mass.

[73] Assignee: The General Hospital Corporation, Boston, Mass.

[21] Appl. No.: 09/132,878

[22] Filed: Aug. 11, 1998

[51] Int. Cl.[7] .................................................. A61B 17/36
[52] U.S. Cl. .................................................. 606/17; 606/9
[58] Field of Search .................................. 606/9, 13–17, 606/1–3; 607/89

[56] References Cited

U.S. PATENT DOCUMENTS

| | | |
|---|---|---|
| 4,122,342 | 10/1978 | Vali et al. . |
| 4,273,127 | 6/1981 | Auth et al. . |
| 4,387,954 | 6/1983 | Beasley . |
| 4,400,056 | 8/1983 | Cielo . |
| 4,447,546 | 5/1984 | Hirschfeld . |
| 4,585,298 | 4/1986 | Mori . |
| 4,660,925 | 4/1987 | McCaughan, Jr. . |
| 4,672,961 | 6/1987 | Davies . |
| 4,693,244 | 9/1987 | Daikuzono . |
| 4,707,201 | 11/1987 | Failes . |
| 4,712,543 | 12/1987 | Baron . |
| 4,799,479 | 1/1989 | Spears . |
| 4,852,567 | 8/1989 | Sinofsky . |
| 4,911,712 | 3/1990 | Harrington . |
| 5,018,842 | 5/1991 | Chen . |
| 5,042,980 | 8/1991 | Baker et al. . |
| 5,122,060 | 6/1992 | Vassiliadis et al. . |
| 5,139,495 | 8/1992 | Daikuzono . |
| 5,207,669 | 5/1993 | Baker et al. . |
| 5,248,311 | 9/1993 | Black et al. . |
| 5,254,114 | 10/1993 | Reed, Jr. et al. ........................ 606/15 |
| 5,342,352 | 8/1994 | Franken et al. . |
| 5,380,318 | 1/1995 | Daikuzono ............................... 606/16 |
| 5,496,309 | 3/1996 | Saadat et al. . |
| 5,498,260 | 3/1996 | Rink et al. . |
| 5,534,000 | 7/1996 | Bruce . |
| 5,707,368 | 1/1998 | Cozean et al. ............................ 606/15 |

FOREIGN PATENT DOCUMENTS

| | | |
|---|---|---|
| 0 400 802 A2 | 12/1990 | European Pat. Off. . |
| 0 529 823 A1 | 3/1993 | European Pat. Off. . |
| 2 154 761 | 9/1985 | United Kingdom . |
| 2 222 881 | 3/1990 | United Kingdom . |
| WO91/02562 | 3/1991 | WIPO . |
| WO95/17924 | 7/1995 | WIPO . |

OTHER PUBLICATIONS

Cox, Jr., "New Method for Exposing Mammalian Cells to Intense Laser Radiation Using the Evanescent Fields Created in Optical Waveguides," *Am. Assoc. Phys. Med.*, 5:274–279, Jul./Aug. 1978.

*Primary Examiner*—Linda C. M. Dvorak
*Assistant Examiner*—Roy Gibson
*Attorney, Agent, or Firm*—Fish & Richardson P.C.

[57] ABSTRACT

The invention features a probe for selectively delivering laser radiation to a first tissue having a first index of refraction relative to a second tissue having a second index of refraction less than the first index. The probe includes a laser transmitting medium having an optical axis and a tissue-contacting surface. In some embodiments, the optical axis contacts the tissue-contacting surface at an angle that is less than the critical angle for an interface between the tissue-contacting surface and the first tissue and greater than or equal to the critical angle for an interface between the tissue-contacting surface and the second tissue, wherein during operation the probe directs the laser radiation along the optical axis to the tissue-contacting surface. In other embodiments, the optical axis forms an angle with the tissue-contacting surface, and during operation the probe directs the laser radiation along the optical axis to the tissue-contacting surface, transmits a first amount of laser energy through the tissue-contacting surface when contacting the first tissue, and transmits a second amount of laser energy through the tissue-contacting surface when contacting the second tissue, wherein the angle is selected such that the first amount of laser energy is at least twice the second amount of laser energy. The invention also features related methods for selectively delivering laser radiation to tissue based on refractive index.

52 Claims, 8 Drawing Sheets

APPARATUS AND METHOD FOR SELECTIVE LASER-INDUCED HEATING OF BIOLOGICAL TISSUE

FIELD OF THE INVENTION

The invention relates to laser surgery and the selective delivery of laser radiation to heat or kill biological tissue.

BACKGROUND OF THE INVENTION

Lasers are useful in medical, materials processing, and other applications to cause ablation, i.e., substance removal, within a substrate, e.g., a biological tissue. In many cases, lasers cause such ablation by rapidly and locally heating a target substance until the target substance vaporizes.

Selective laser ablation can be accomplished by using laser wavelengths that are strongly absorbed by the target tissue and only weakly absorbed by other tissue. Thus, the target tissue absorbs an amount of laser energy above a threshold for laser ablation and is removed, whereas the other tissue absorbs an amount of laser energy below the threshold and remains. However, many medical lasers and delivery systems currently available do not always operate at wavelengths that are absorbed substantially more by some types of tissue and not by other types of tissue.

SUMMARY OF THE INVENTION

The invention is based on the discovery that laser radiation can be selectively delivered or coupled into a first material or substrate, e.g., a first biological tissue, having a first index of refraction and not delivered into a second material or substrate, e.g., a second biological tissue, having a second index of refraction less than the first index of refraction, by using a specially designed probe that delivers the laser radiation. When the new probe contacts biological tissue, the probe delivers the laser radiation to the tissue at an angle of incidence that allows for selective transmission of the laser radiation to the tissue based on its index of refraction.

The new probe can be used to selectively remove fat-containing tissue, which typically has an index of refraction greater than that of tissue such as muscle, which has a substantial water content. Fat-removal can be important in procedures such as laser liposuction, laser angioplasty, and dissection of fat. In these and other applications, it is important that the laser efficiently ablate the target tissue (e.g., fat) while producing little or no damage to other tissue (e.g., muscle or skin).

The laser radiation delivered to the selected tissue can rapidly heat the selected tissue until it vaporizes, thereby removing, ablating, or killing the selected tissue. Alternatively, the laser radiation delivered to the selected tissue can rapidly heat the selected tissue until it melts. Thereafter, the melted tissue is removed using suction or other methods.

In general, in one aspect, the invention features a probe for selectively delivering laser radiation to a first substrate such as a tissue having a first index of refraction relative to a second substrate (tissue) having a second index of refraction less than the first index. The probe includes a laser transmitting medium including an optical axis and a substrate-contacting, e.g., tissue-contacting, surface. The optical axis contacts the tissue-contacting surface at an angle that is less than the critical angle for an interface between the tissue-contacting surface and the first tissue and greater than or equal to the critical angle for an interface between the tissue-contacting surface and the second tissue, wherein during operation the probe directs the laser radiation along the optical axis to the tissue-contacting surface.

In another aspect, the invention features an additional probe for selectively delivering laser radiation to a first tissue having a first index of refraction relative to a second tissue having a second index of refraction less than the first index. The probe includes a laser transmitting medium including an optical axis and a tissue-contacting surface, the optical axis forming an angle with the tissue-contacting surface. During operation, the probe directs the laser radiation along the optical axis to the tissue-contacting surface, transmits a first amount of laser energy through the tissue-contacting surface when contacting the first tissue, and transmits a second amount of laser energy through the tissue-contacting surface when contacting the second tissue. The angle is selected such that the first amount of laser energy is at least twice, and in some embodiments at least four times, the second amount of laser energy.

Embodiments for either of the probes described above can include any of the following features.

The angle can be substantially equal to a principle angle for optimal transmission when the tissue-contacting surface contacts the first tissue. The first tissue can consist essentially of fat and the second tissue can consist essentially of muscle, blood vessels, or skin. The first index of refraction can be greater than 1.4 at the wavelength of the laser radiation.

The probes can further include an optical fiber defining the optical axis, wherein during operation the fiber directs the laser radiation to the tissue-contacting surface. The probes can further include a prism connected to an end of the optical fiber, wherein during operation the fiber directs the laser radiation into the prism through a first face of the prism and towards a second face of the prism, the second face of the prism forming the tissue-contacting surface. In some embodiments, the laser radiation reflected from the second face of the prism can propagate along a path within the prism that is substantially normal to a third face of the prism having a reflective coating. In other embodiments, the probes can further include a second fiber, and the second and one or more additional faces of the prism direct laser radiation reflected from the second face to the second fiber, which carries the reflected radiation away from the prism.

The invention also features an apparatus that includes the probe and a laser radiation source coupled to the probe for delivering the laser radiation to the probe. The laser radiation source can include a diode laser, Nd:YAG laser, CTE:YAG laser, ErCr:YSGG laser, holmium laser, erbium laser, $CO_2$ laser, or dye laser.

In a further aspect, the invention features a method for selectively delivering laser radiation to a first tissue relative to a second tissue in which the first tissue has a first index of refraction and the second tissue has a second index of refraction that is less than the first index of refraction. The method includes contacting the first tissue in the patient with a probe; and delivering the laser radiation to the patient through the probe at a first angle of incidence greater than the critical angle for an interface between the probe and the second tissue.

The method can further include redirecting laser radiation reflected from the first tissue or second tissue in the patient back to the tissue at a second angle of incidence substantially equal to the first angle of incidence. Alternatively, the method can further include directing laser radiation reflected from the first tissue or second tissue in the patient away from the patient.

In another aspect, the invention features an additional method for selectively delivering laser radiation to a first tissue in a patient relative to a second tissue in which the first tissue has a first index of refraction and the second tissue has a second index of refraction that is less than the first index of refraction. The method includes contacting the patient with a probe; and delivering the laser radiation to the patient through the probe at an angle of incidence such that the energy transmitted into the first tissue when the probe contacts the first tissue is at least twice, and in some embodiments, at least four times, the energy transmitted into the second tissue when the probe contacts the second tissue.

Biological tissue is solid tissue from, or in, a human, animal, or plant. Fat-containing tissue is biological tissue characterized by a relatively high lipid concentration including, for example, subcutaneous fat, lipomas, liposarcomas, arteriosclerotic fat, granulomas, xanthelasmas, xanthomas, intraperitoneal fat, and retroperitoneal fat. Biological tissue that contains little or no fat includes, for example, muscle, skin, blood vessels, other organs, and cartilage. At some wavelengths, the refractive index of other tissues, e.g., bone, teeth, and calculi (stones), is greater than that of fat. When desired, embodiments of the invention can be used to selectively affect, e.g., ablate, these high-index tissues.

The critical angle $\theta_c$ for a probe/substrate interface is defined by $\theta_c = \sin^{-1}(n'/n)$, where n is the refractive index of the probe, n' is the refractive index of the substrate, and the substrate can be absorbing or non-absorbing. In the latter case, the critical angle corresponds to the angle for total internal reflection (TIR).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention has many advantages. For example, the probe can selectively deliver or couple laser radiation to biological tissue. Thus, selected tissue, e.g., fat-containing tissue, can be ablated or melted, while adjacent tissue, e.g., muscle, is left unharmed. Also, the probe can be used in a large number of surgical procedures, e.g., open surgery, subcutaneous procedures, endoscopic procedures, catheter procedures, and arteriosclerotic procedures. Furthermore, since there are many wavelengths at which different types of biological tissues have substantially different indices of refraction, the probe can be used with many readily available laser sources that operate at such wavelengths. For example, the probe can be used with a holmium laser operating at a wavelength of 2.1 microns, a diode or dye laser operating in the visible to near-infrared region, a $CO_2$ laser operating in the infrared region, an Er:YSGG laser operating at a wavelength of 2.79 microns and other erbium lasers operating between wavelengths of 2.5 and 3.0 microns, thulium lasers operating at wavelengths between 1.94 to 2.01 microns, a CTE:YAG laser, and a ErCr:YSGG laser, the latter two lasers operating at wavelengths of about 2.7 microns.

Other features and advantages of the invention will be apparent from the following detailed description, and from the claims.

BRIEF DESCRIPTION OF THE DRAWING

FIGS. 6, 7, and 8 are graphs showing percent reflectance from a tissue/probe interface as a function of incident angle for muscle tissue (solid line) and fat tissue (dashed line). FIG. 6 is for a fused silica probe and 2.69 micron wavelength radiation, FIG. 7 is for a sapphire probe and 2.69 micron wavelength radiation, and FIG. 8 is for a flint glass probe and 2.13 micron wavelength radiation.

DETAILED DESCRIPTION

The invention features a surgical probe that has a surface configured to contact a material, such as biological tissue, and that carries laser radiation within the probe to the probe surface at an angle of incidence different from normal incidence. When the probe surface contacts biological tissue, the fraction of laser energy transmitted to the biological tissue from the probe will depend on the angle of incidence, the polarization of the laser radiation, the index of refraction of the probe, the index of refraction of the tissue, and the absorption of the tissue.

The probe is designed to selectively transmit a substantial portion, e.g., greater than 50%, of the laser radiation through the probe surface to the biological tissue if that tissue has an index of refraction greater than a threshold value, and to reflect a substantial portion, e.g., greater than 50%, of the laser radiation from the surface if the tissue has an index of refraction less than that threshold value. The shape and structure of the probe can be varied to provide a threshold value suitable to selectively distinguish between particular types of tissues. In specific embodiments, the probe can be designed to selectively transmit laser radiation to fat-containing tissue, and not to other types of tissue such as muscle, skin, blood vessels, and organs, which have an index of refraction lower than that of fat-containing tissue.

General System

Figure 1:
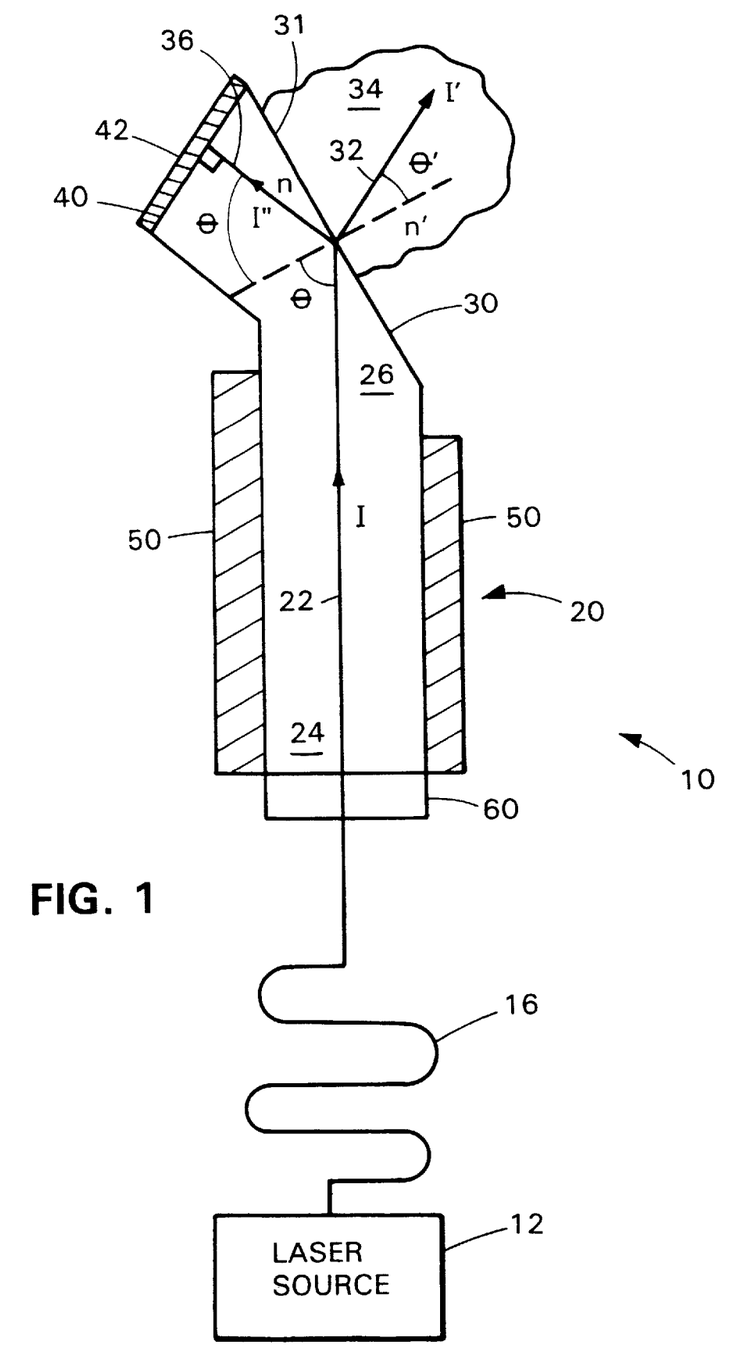
FIG. 1 is a schematic of a system for selectively delivering laser radiation to a material such as a tissue.

FIG. 1 shows a system 10 for selectively delivering laser radiation from a source 12 to a specific biological tissue 34. Optical fiber 16, or some other optical delivery mechanism, e.g., mirrors, waveguides, or articulated arms, guide laser radiation having wavelength $\lambda$ from source 12 to the proximal end 24 of a laser radiation delivery probe 20. The probe has a shape and structure that allows the laser radiation to propagate within the probe along a path 22, which forms an angle $\theta$ with a surface 30 at the distal end 26 of probe 20. Surface 30 is substantially planar extending perpendicular to the plane of FIG. 1, and is designed to contact, and form an interface 31 with, biological tissue 34, as shown in FIG. 1.

Upon striking interface 31, the laser radiation having an irradiance I, splits into a first portion having an irradiance I', which transmits through the interface into tissue 34 along a refracted path 32 that forms an angle $\theta'$ with interface 31, and a second portion having an irradiance I", which reflects from surface 30 and propagates within probe 20 along a reflected path 36. The relative energies I'/I and I"/I depend on the indices of refraction n and n' for probe 20 and biological tissue 34, respectively, the wavelength $\lambda$, the angle of incidence $\theta$, the polarization of the laser radiation, and the absorption at wavelength $\lambda$ of biological tissue 34.

For the specific wavelength $\lambda$, the index of refraction n and angle of incidence $\theta$ defined by probe 20 are such that the transmitted energy $I_{n1'}$ when surface 30 contacts tissue 34, e.g., fat, having an index n'=$n_1$' is substantially larger than the transmitted energy $I_{n2}$, when the surface 30 contacts tissue 34, e.g., muscle, having an index n'=$n_2$', where $n_1$'>$n_2$'. For example, in many cases $I_{n1}$/$I_{n2}$, is greater than about 2, in some cases $I_{n1}$/$I_{n2}$, is greater than about 4, and in further cases $I_{n1}$/$I_{n2}$, is greater than about 10. The selectivity of the probe is proportional to this ratio.

In some embodiments, probe 20 delivers laser radiation such that the angle of incidence θ defined when surface 30 contacts tissue 34 is less than a critical angle for tissue 34 having an index n'=$n_1$', and greater than a critical angle for tissue 34 having an index n'=$n_2$', wherein the critical angle $\theta_c$ for tissue 34 is defined by:

$$\theta_c = \sin^{-1}(n'/n) \quad (1)$$

where n is the refractive index of probe 20 and n' is the refractive index of tissue 34. In many such cases, the laser radiation is substantially reflected by the tissue having the index n'=$n_2$' and only partially, if at all, reflected by the tissue having the index n'=$n_1$'. This is especially true for tissues that do not absorb, or only weakly absorb, the wavelength of the laser radiation. In particular, for non-absorbing tissues, the critical angle $\theta_c$ is the angle at which total internal reflection (TIR) occurs for light propagating from a high-index medium (the probe) to a low-index medium (the tissue). In such cases, the laser radiation is totally reflected by the tissue having the index n'=$n_2$'.

Furthermore, since the angle of incidence is greater than the critical angle for the low index tissue, it will also be greater than the critical angle for a probe/air interface, since air has a refractive index equal to about 1. Thus, when the probe is not contacting any tissue, the laser radiation undergoes total internal reflection from the probe/air interface, thereby preventing accidental delivery of laser radiation to non-target tissue.

Mathematical Description and Probe Design

In general, the relative energy I"/I reflected by tissue 34 when contacted by surface 30 of the probe is determined by decomposing the incident laser radiation I into its parallel and perpendicular polarization components and using the Fresnel equations shown below:

$$R_\perp = \left| \frac{n\cos\theta - [(n'-ik')^2 - n^2\sin^2\theta]^{1/2}}{n\cos\theta + [(n'-ik')^2 - n^2\sin^2\theta]^{1/2}} \right|^2 \quad (2)$$

$$R_\| = \left| \frac{(n'-ik')^2\cos\theta - n[(n'-ik')^2 - n^2\sin^2\theta]^{1/2}}{(n'-ik')^2\cos\theta + n[(n'-ik')^2 - n^2\sin^2\theta]^{1/2}} \right|^2 \quad (3)$$

where $R_\|$ and $R_{195}$ are the relative reflectances for parallel and perpendicular polarizations, respectively, n' and k' are the real and imaginary parts, respectively, of the complex refractive index for tissue 34, n is the refractive index of probe 20, which is assumed to be non-absorbing, or negligibly absorbing, and θ is the angle of incidence. The incident laser radiation I may be polarized, e.g., by polarizer 60 in FIG. 1, parallel, perpendicular, or some intermediate polarization, and it may also be randomly polarized (in which case on average it has equal energies of parallel and perpendicular polarizations).

Note that the imaginary part of the refractive index, k, can be related to the absorption coefficient α used in the well-known Lambert's law for absorption of light irradiance I propagating through an absorbing medium along an axis x, i.e., I(x)=I(x=0)*exp(-αx), by α=4 πk/λ.

Eqs. 2 and 3 above can be used to calculate the effectiveness of a probe characterized by a refractive index n and an angle of incidence θ for selectively delivering laser radiation to different types of solid, biological tissue based on their different refractive indices. In addition, these equations can be used to determine optimal parameters, n and θ, to design a probe that substantially delivers laser radiation to a first type of biological tissue having a refractive index $n_1$', e.g., fat, and not to a second type of biological tissue having a refractive index $n_2$', e.g., muscle.

For example, in cases where absorption by the biological tissues can be ignored, i.e., k'<<n', a probe having parameters n and θ that satisfy $$n_1' > n \sin\theta > n_2' \quad (4)$$

will produce total internal reflection from the second type of tissue while delivering at least some laser radiation to the first type of tissue. Even in cases where the biological tissue is only weakly absorbing, e.g., k'/n'<0.01, the reflection from the second type of tissue for a probe satisfying Eq. 4 is typically greater than 80%.

In addition to designing the probe with an n and θ that increase, and in some cases maximize, reflection from the second type of biological tissue, the reflection from the first type of biological tissue should be decreased, and in some cases minimized. For example, for parallel polarized light there is a minimum in reflection for some intermediate angle θ, known as a the principle angle. In particular, if absorption is negligible, i.e., take k'=0, Eq. 4 shows that when θ=$\tan^{-1}(n_2'/n_1')$, $R_\| = 0$.

Examples of calculations using Eqs. 2 and 3 to design the probe such that it is especially suitable for selectively delivering laser radiation to fat and not to muscle are described below.

Probe Shapes and Structures

Probe 20 can have a variety of shapes and can be made from a variety of materials. What is important is that probe 20 receives laser radiation from source 12 and carries that laser radiation along an internal path, e.g., path 22, that intersects the tissue-contacting surface 30 with a suitable angle of incidence, θ, as shown in FIG. 1. As described above, the angle θ and index n of probe 20 determine which types of tissue 34 selectively receive laser radiation from probe 20.

It is also important that laser radiation internally reflected from surface 30 does not undergo additional reflections within probe 20 that redirect the laser radiation back to surface 30 at an angle different from the angle θ. If this were the case, transmission of the redirected radiation through surface 30 could undermine the selectivity provided by the initial interaction of the laser radiation with surface 30.

To prevent laser radiation internally reflected within probe 20 from being incident on surface 30 at angles other than θ, probe 20 includes an additional surface 40 that is substantially normal to the reflected laser radiation. Like surface 30, surface 40 is substantially planar, extending perpendicular to the plane of FIG. 1. Laser radiation propagates along path 22, intersects surface 30 with an angle of incidence equal to θ, and that radiation reflected from surface 30 reflects from the surface with an angle equal to θ. As shown in FIG. 1, the reflected radiation then propagates within probe 20 along a path 36 towards surface 40. Since surface 40 is substantially normal to path 36, laser radiation reflected from surface 40 propagates back along path 36 towards surface 30. This retroreflected laser radiation again intersects surface 30 with an angle of incidence equal to θ, and thereby delivers laser radiation to tissue 34 with the same selectivity as the first pass. Laser radiation reflected from surface 30 a second time propagates back along path 22 towards fiber 16, where it can be absorbed or reflected back to surface 30. Surface 40 can include a reflective coating 42, e.g., a thin metal film for the case of visible or infrared laser radiation, which insures that the laser radiation only exits distal end 26 of the probe through surface 30. Alternatively, in place of the reflective coating, surface 40 can include an adjacent absorber or diffuser that dissipates the laser radiation.

As shown in FIG. 1, the elongate portion of probe 20 along path 22 can be surrounded by a housing 50 that only exposes distal end 26 of the probe to tissue 34. Also, in other embodiments, the housing can surround surface 40 so that only the tissue contacting surface 30 is exposed to tissue 34. Housing 50 provides mechanical stability to probe 30, and may be used as a handle if the probe is manipulated manually by a surgeon. Alternatively, housing 50 can also provide a mechanical connection to a device, e.g., a catheter guide wire or an endoscopic medical instrument, when the probe is used internally in a patient and manipulated at a distance by a surgeon.

In various embodiments, the portion of probe 20 that provides path 22 can be shorter or longer than that shown in FIG. 1, and probe 20 can be wider or thinner than that shown in FIG. 1. The precise dimensions depend on the specific application. For example, for open surgical procedures, the diameter of tissue-contacting surface 30 may be in the range of about 2 mm to 1 cm, whereas for angioplasty applications, the diameter may on the order of about 0.5 to 3.0 mm. Another example is endoscopic or laparoscopic surgery in which fatty tissue adherent to bowel or other delicate structure can be ablated. Bone, teeth, and calculi (e.g., kidney stones) also have higher refractive indices than adjacent fleshy tissue and can also be treated.

Figure 2:
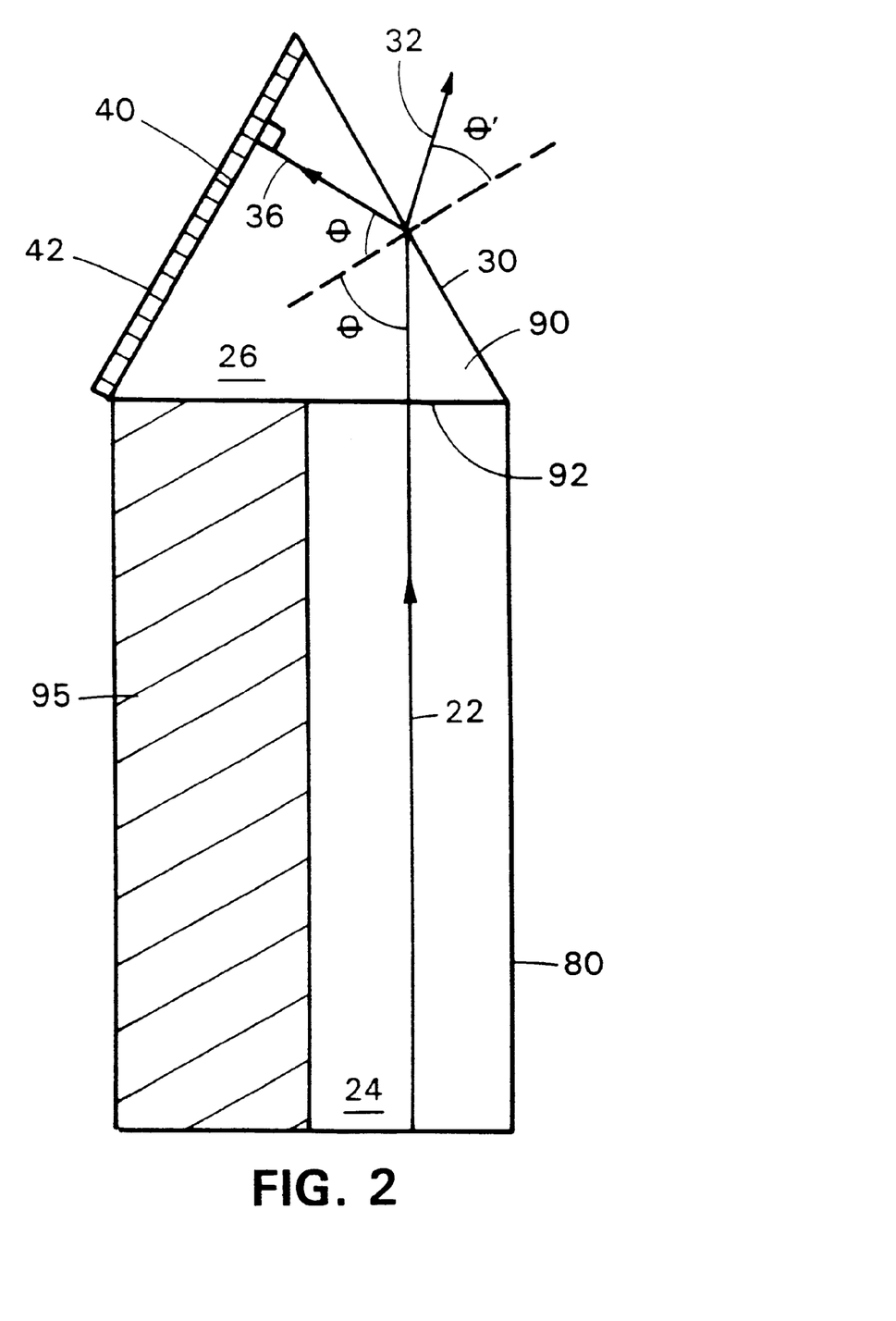
FIGS. 2, 3, 4 and 5 are schematics of different embodiments of a probe for selectively delivering laser radiation to specific tissues.

In some embodiments, probe 20 includes an optical fiber and a prism. For example, as shown in FIG. 2, an optical fiber 80 forms the distal end 24 of probe 20 and a prism 90 connected to fiber 80 forms the proximal end 26 of probe 20. The prism connects to the fiber at a surface 92 and also includes tissue-contacting surface 30 and surface 40. The laser radiation propagates within fiber 80 along path 22, which is along the length of the fiber, and into prism 90, where it intersects the tissue-contacting surface 30 at an angle of incidence θ and is selectively transmitted to the tissue along path 32. Laser radiation reflected from surface 30 propagates within prism 30 along path 36, which intersects surface 40 at normal incidence. Surface 40 retroreflects the laser radiation back along path 36.

Prism 90 and optical fiber 80 can be made of the same material or different materials as described herein. If they are made of different materials, index-matching fluid can be used where they connect to prevent reflections from surface 92. If necessary, a support block 95 connected to prism 90 and fiber 80 can be used to provide mechanical support to the prism 90. Prism 90 in FIG. 2 is an equilateral prism with angles of 60° in which case the angle of incidence θ also equals 60°.

Figure 3:
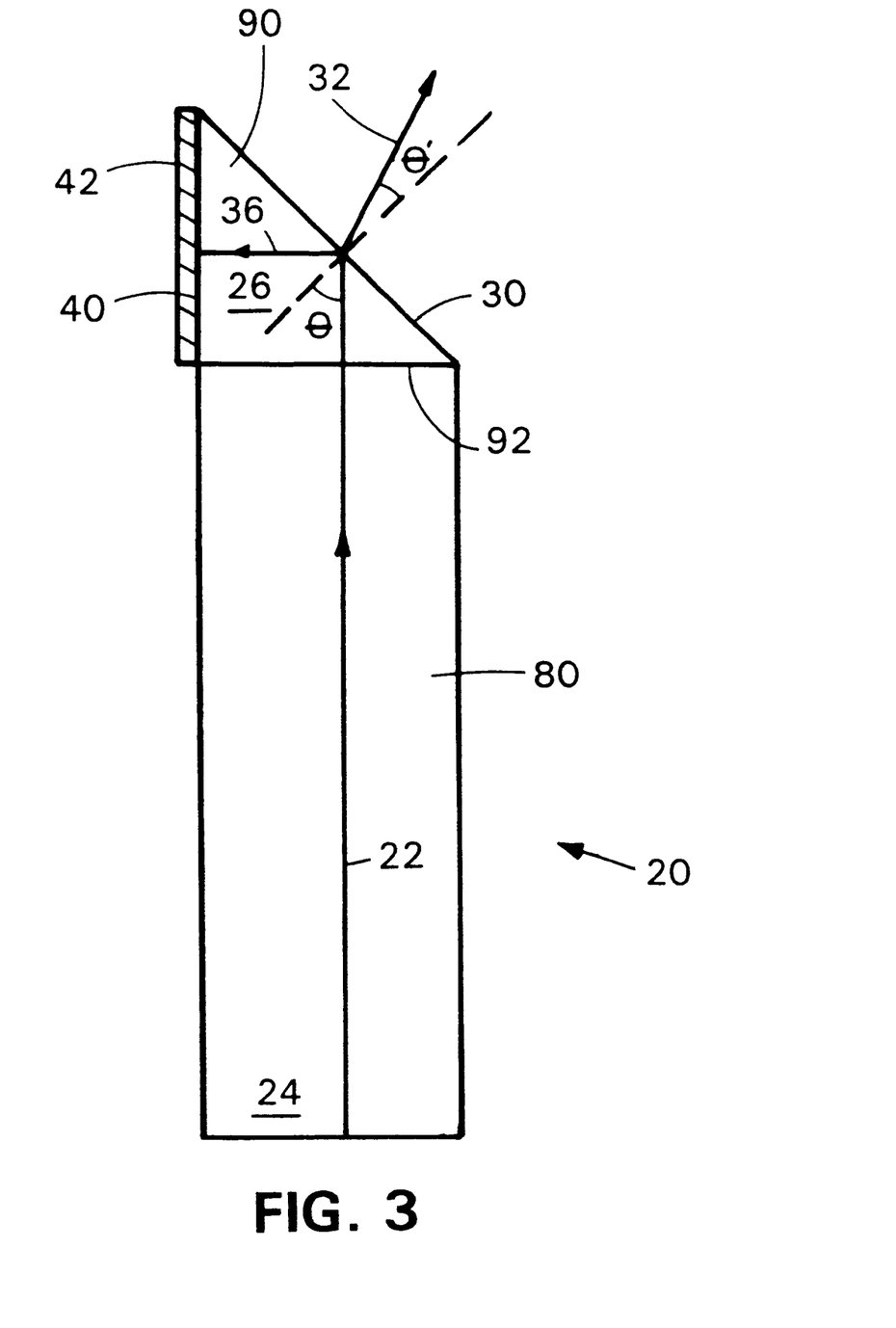

In other embodiments, prisms with different shapes and angles can also be used. For example, in FIG. 3, prism 90 is shown having angles of 45, 45, and 90 degrees and an angle of incidence θ equal to 45 degrees. As in the design shown in FIG. 2, laser radiation reflected from surface 30 propagates within prism 30 along path 36, which intersects surface 40 at normal incidence, and surface 40 retroreflects the laser radiation back along path 36. Such prisms made from, e.g., flint, BK7 glass, sapphire, or fused silica, are useful to selectively ablate fat over muscle at wavelengths between, e.g., 2 to 3 microns, as shown in the examples further below.

Figure 4:
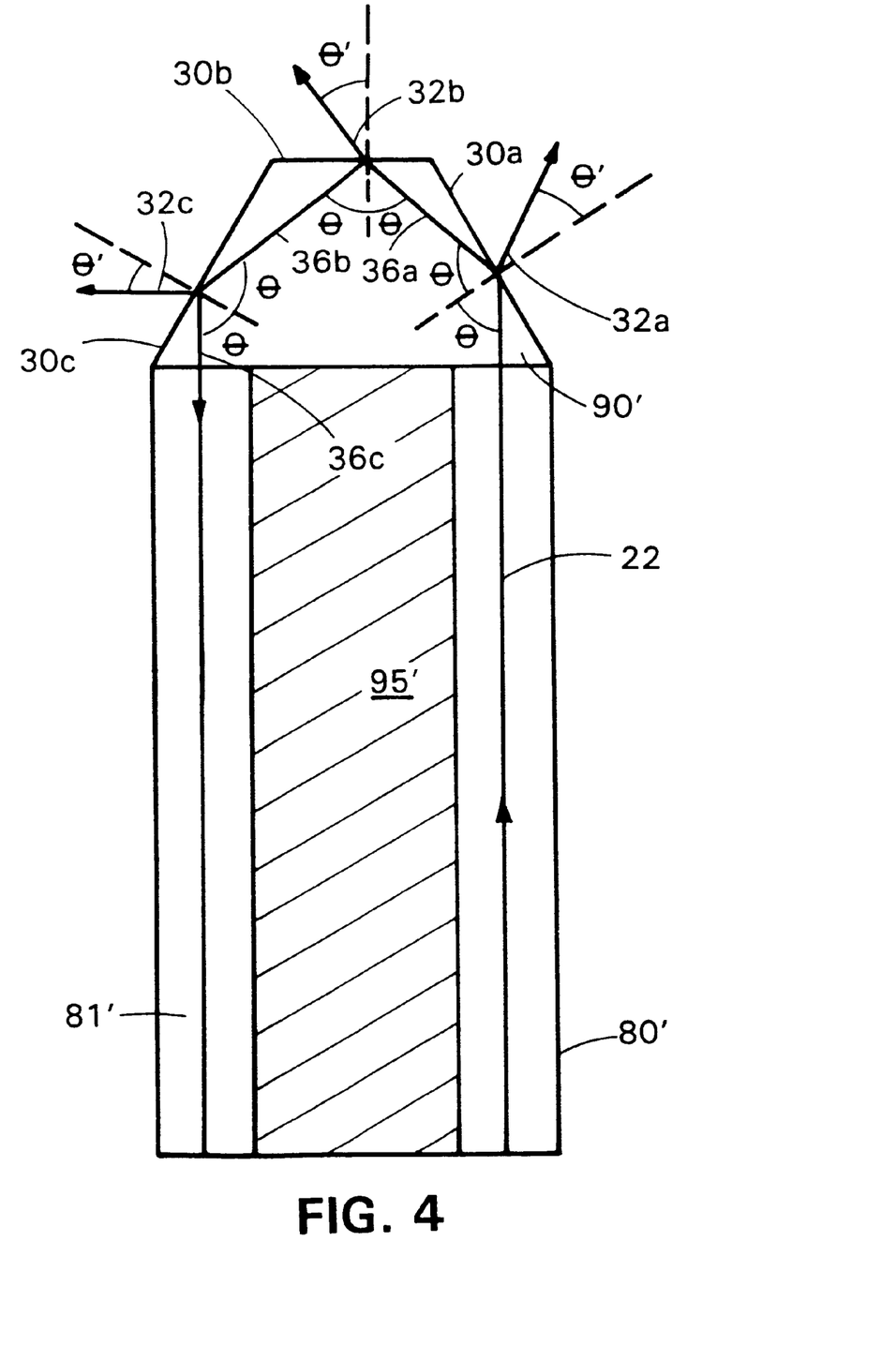

In another embodiment shown in FIG. 4, probe 20 can include a non-triangular prism 90', an input fiber 80', and an output fiber 81'. In this embodiment, prism 90' includes three surfaces 30a, 30b, and 30c, each of which can be used as the tissue contacting surface. Laser radiation is delivered to prism 90' along path 22 in fiber 80' and intersects surface tissue-contacting surface 30a at an angle of incidence θ, where it is selectively transmitted to the tissue along path 32a. Laser radiation reflected from surface 30a propagates within prism 30' along path 36a, which intersects surface 30b at an angle of incidence also equal to θ, where it can be selectively transmitted to the tissue along path 32b. Laser radiation reflected from surface 30b propagates within prism 30' along path 36b, which intersects surface 30c at an angle of incidence also equal to θ, where it can be selectively transmitted to the tissue along path 32b. Laser radiation reflected from surface 30c propagates within prism 30' along path 36c, which directs the reflected radiation into the output fiber 81' where it is carried away from the biological tissue.

In this embodiment, prism 90' is formed such that surfaces 30a, 30b, and 30c make angles of 30°, 90°, and −30° with the axis of the input and output fibers and thereby the angle of incidence θ equals 60°. Such a prism can be formed from an equilateral triangular prism that has an upper equilateral portion removed from it. A mechanical support 95' can be placed between input and output fibers 80' and 81'.

Figure 5:
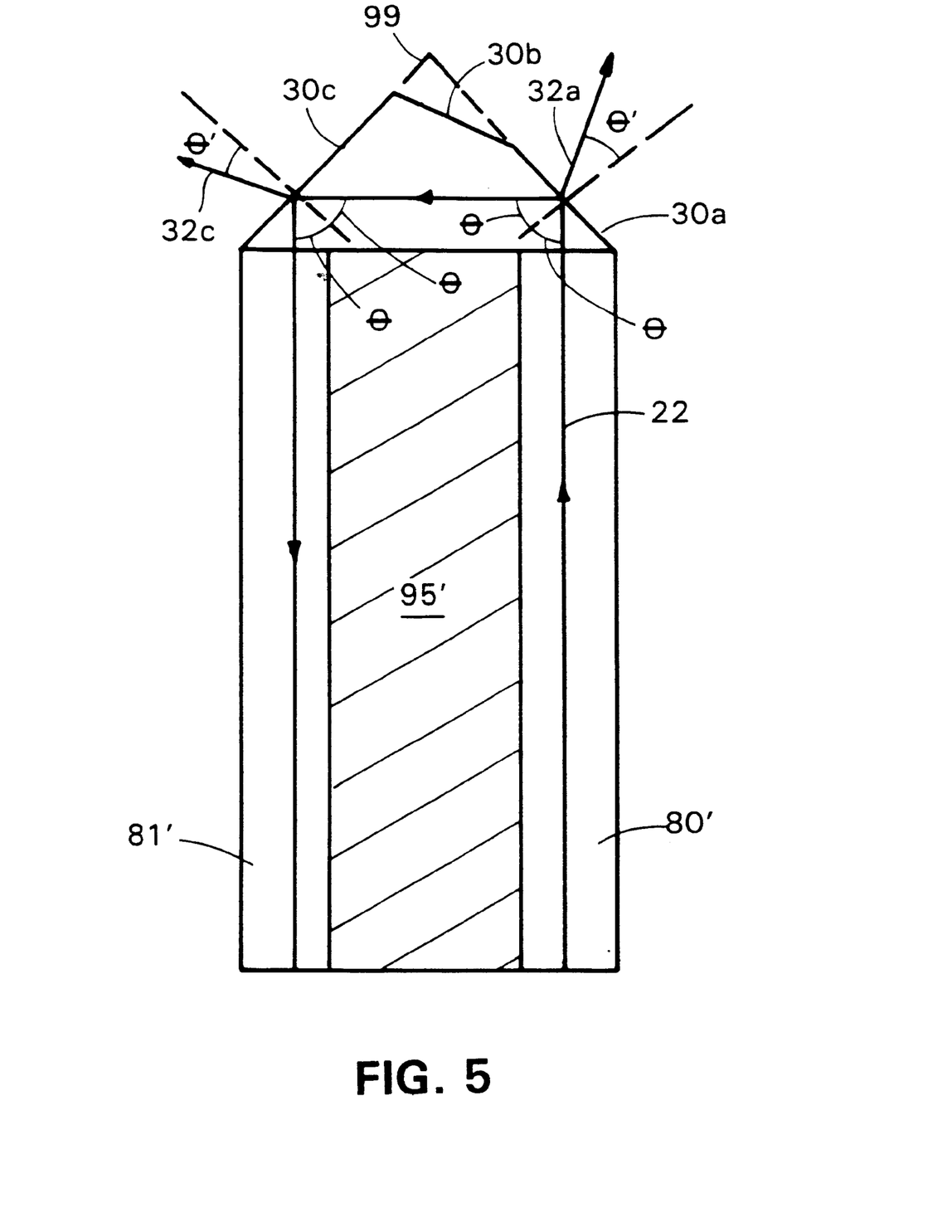

In a similar embodiment shown in FIG. 5, prism 90' is formed such that surfaces 30a and 30c make angles of 45° with both the axes of the input and output fibers, and the angle of incidence of the laser radiation with respect to these surfaces is also 45°. In this embodiment, the laser radiation does not intersect surface 30b. Such a prism can be formed from a triangular prism having angles of 45, 45, and 90 degrees in which a portion adjacent the 90° angle is removed to form surface 30b. Alternatively, since the laser radiation does not intersect surface 30b, the portion adjacent the 90° angle need not be removed, as indicated by dashed line 99 in FIG. 5.

In other embodiments, rather than attach a prism to the proximal end of a fiber, the proximal end of the fiber itself can be polished to provide the appropriate tissue contacting surface. Other embodiments are also possible, for example, the embodiments of FIGS. 4 and 5 may have circular symmetry about an axis between the input and output fibers so that the input and output fibers are both parts of an annular waveguide that directs laser radiation to a conical prism. In such a case, the tissue-contacting surfaces are curved.

The prism and fiber used in the above embodiments can be made from a number of materials known in the art. For example, the fiber can be made from silica glasses, preferably those having relatively few hydroxy (OH) bonds that can lead to absorption of the laser radiation, and other materials that do not absorb the laser radiation, e.g., flint, plastics, sapphire, and liquid-filled fibers. The portion of the probe contacting the tissue at surface 30, e.g., the prism or fiber, can be made from materials including, for example, fused silica, sapphire, silicon, germanium, flint glass, BK7 glass, and zinc selenide.

Laser Sources, Wavelengths, and Uses

Suitable sources for the laser radiation include, for example, those lasers operating at wavelengths in the visible and infrared regions, including, e.g., diode lasers, Nd:YAG lasers, holmium lasers, erbium lasers, thulium lasers, CTE:YAG lasers, dye lasers, and $CO_2$ lasers.

Particular wavelengths that may be suitable include wavelengths in the range of about 400 to 550 nm, where dye lasers operate and where there is substantial absorption by fat, wavelengths of about 1.7 microns where there is also substantial absorption by fat, wavelengths of about 2.7 microns where the index of refraction for water is near a minimum, and wavelengths of about 10.6 microns where commercial $CO_2$ laser operate. Additional wavelengths can include 2.13 microns where commercially available Holmium:YAG lasers operate and around 2.7 microns where CTE:YAG and ErCr:YSGG lasers operate.

The precise shape, size, and material for the probe depends on the refractive and absorptive properties of the tissues to which the laser radiation is to be selectively delivered, the wavelength of that laser radiation, and the method of surgery. Referring again to FIG. 1, system 10 selectively delivers laser radiation to target tissue, and melts or vaporizes the target tissue. The wavelength of the laser radiation provided by source 12 is absorbed by, and thereby heats, the target tissue. For example, to vaporize fat-containing tissue with the laser radiation, the wavelength of the laser radiation could be within an absorption band of the fat-containing tissue. After a sufficient exposure, the laser radiation vaporizes or melts the fat-containing tissue. Alternatively, the wavelength of the laser radiation could be outside the absorption bands of the fat-containing tissue, but within the absorption bands of water contained within the fat-containing tissue. In such a case, the probe/fat interface allows the laser radiation to propagate into the fat whereupon the water contained therein absorbs the radiation and heats the fat-containing tissue until it vaporizes or melts. In contrast, a probe/muscle interface substantially prevents laser radiation from propagating into the muscle even though it is a water-rich tissue. Regardless of the mechanism, melted fat tissue can be removed from a patient through suctioning. The fluence necessary for ablation or melting can be estimated from known parameters including transmission into tissue, tissue absorption, tissue absorption coefficient, heat capacity, and pulse width.

The wavelength of the laser radiation provided by source 12 in system 10 specifies the indices of refraction of the target and adjacent tissues. For the probe to selectively deliver the laser radiation to the target tissue and not adjacent tissue, the index of refraction of the target tissue $n_1$ must be greater than the index of refraction of the adjacent tissue $n_2$. If this condition is specified, suitable values for the index of refraction n and the angle of incidence $\theta$ defined by probe 20 can be determined from Eq. 4, for the case of total internal reflection and negligible tissue absorption, or more generally from Eqs. 2 and 3. The precise index of refraction for possible probe materials and biological tissues can be determined at a number of wavelengths using optical techniques well known in the art, such as internal reflection spectroscopy, refractometry, optical retardation, and reflectance. See, for example, N. J. Harrick, *Internal Reflection Spectroscopy* (Harrick Scientific Corp., Ossining N.Y., 1987).

The size of probe 20 will depend on the particular application. In some embodiments, probe 20 is a hand-held device for use in open or minimally invasive surgery. In other embodiments, probe 20 connects to the end of an endoscope or a catheter placed within the patient and is manipulated by the surgeon with additional tools. For example, the probe can be inserted into blood vessels using a catheter guide wire to remove fatty deposits, e.g., arteriosclerotic fat, from therein.

The probe is particularly useful for selectively delivering laser radiation to fat-containing tissue and not to adjacent tissue such as muscle, skin, blood vessels, cartilage, and organs. The fat-containing tissue can be exposed for a period sufficient to melt and/or vaporize the fat-containing tissue. The melted fat can be removed by subsequent suctioning. Particular types of fat-containing tissue that can be removed by the probe include: subcutaneous fat; lipomas or liposarcomas, which are benign and malignant tumors of fat, respectively; arteriosclerotic fat, including fatty lesions prior to calcification; granulomas; xanthelasmas and xanthomas, which are fatty deposits within the skin and common within eyelids; and intraperitoneal and retroperitoneal fat, which may de removed during dissections and/or during abdominal surgery.

The invention is illustrated by the following simulated examples, which do not limit the claimed invention.

EXAMPLE 1

In this example, the reflectance from muscle and fat tissues were calculated as a function of incident angle based on Eqs. 2 and 3 for the case of 2.69 micron wavelength radiation produced by a CTE:YAG laser and delivered to the tissue through a fused silica prism. The following parameters for refractive index n and absorption k at 2.69 microns were used: $n_1$ (fat)=1.42; $n_2$ (muscle)=1.185; $k_1=k_2=0.0145$; and n (fused silica)=1.436. The laser radiation was taken as perpendicularly polarized. The relative reflectance for fat (dashed line) and muscle (solid line) are shown in FIG. 6.

Figure 6:
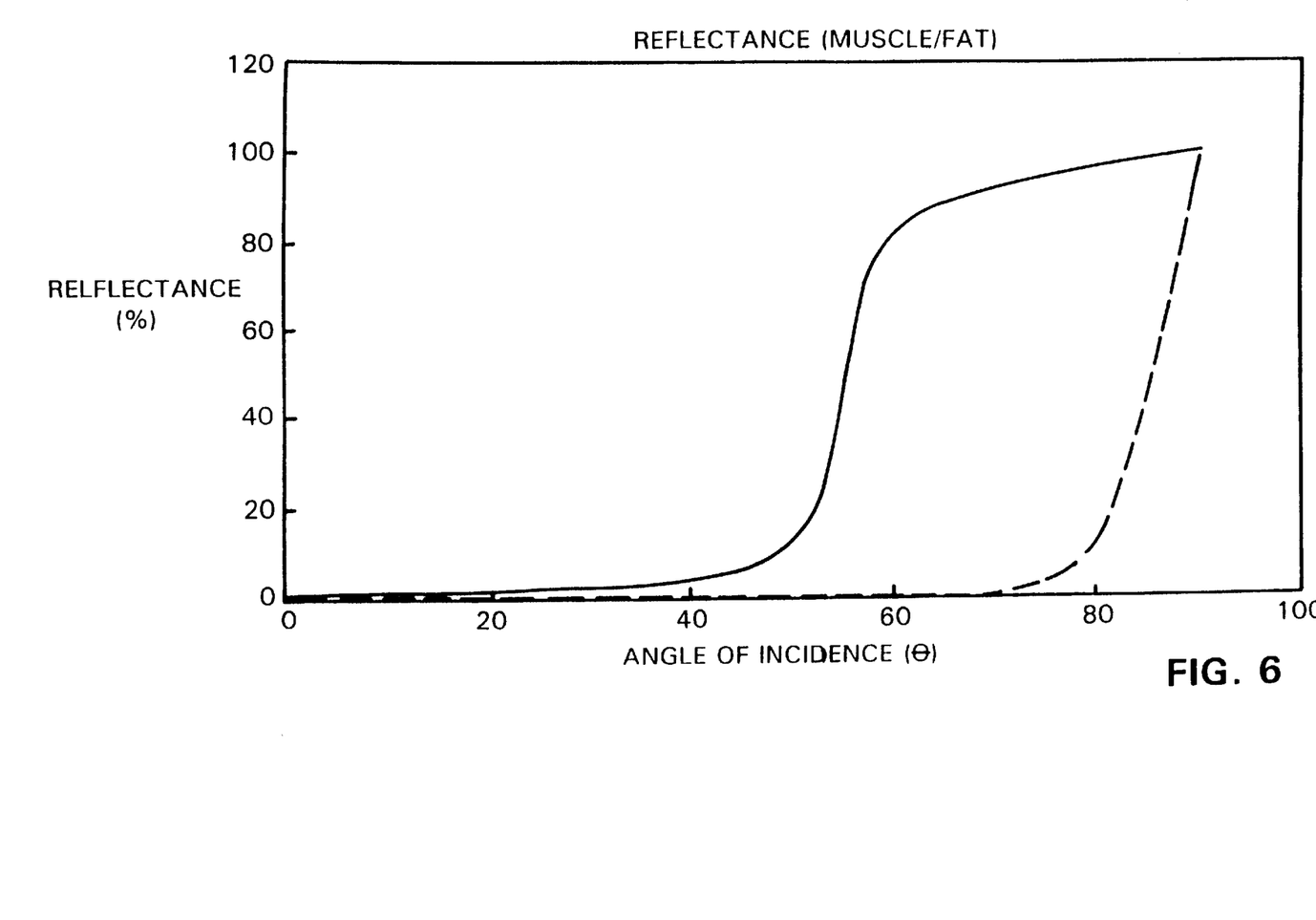

As shown in FIG. 6 there is substantial selectivity for incident angles between about 55° and 80°. In particular, at an incident angle of 60°, the reflectivity from muscle tissue is about 82%, whereas the reflectivity from fat tissue is about 0.1%. Thus, a probe similar to that of FIGS. 2 or 4 (those that have an incident angle of 60°) having a fused silica prism and a 2.69 micron source from a CTE:YAG laser will be suitable to selectively deliver laser radiation to fat and not muscle.

EXAMPLE 2

In this example, the reflectance from muscle and fat tissue were calculated as a function of incident angle based on Eqs. 2 and 3 for the case of 2.69 micron wavelength radiation produced by a CTE:YAG laser and delivered to the tissue through a sapphire prism. The following parameters for refractive index n and absorption k at 2.69 microns were used: $n_1$ (fat)=1.42; $n_2$ (muscle)=1.185; $k_1=k_2=0.0145$; and n (sapphire)=1.738. The laser radiation was taken as perpendicularly polarized. The relative reflectance for fat (dashed line) and muscle (solid line) are shown in FIG. 7.

Figure 7:
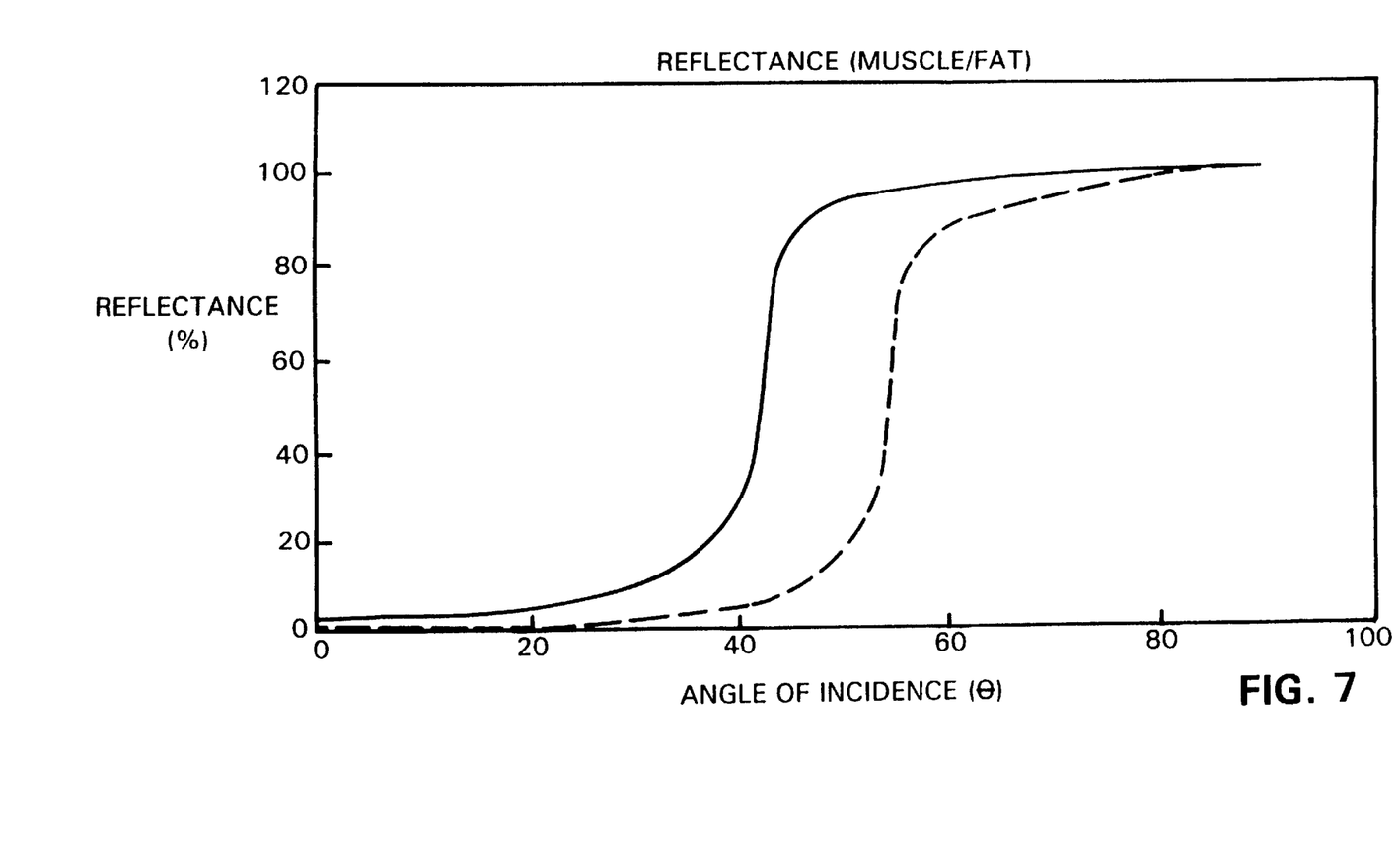

As shown in FIG. 7 there is substantial selectivity for incident angles between about 40° and 50°. In particular, at an incident angle of 45°, the reflectivity from muscle tissue is about 86%, whereas the reflectivity from fat tissue is about 7%. Thus, a probe similar to that of FIGS. 3 or 5 (those that have an incident angle of 45°) having a sapphire prism and a 2.69 micron source from a CTE:YAG laser will be suitable to selectively deliver laser radiation to fat and not muscle.

EXAMPLE 3

In this example, the reflectance from muscle and fat tissue were calculated as a function of incident angle based on Eqs. 2 and 3 for the case of 2.13 micron wavelength radiation produced by a Holmium:YAG laser and delivered to the tissue through a flint glass prism. The following parameters for refractive index n and absorption k at 2.13 microns were used: $n_1$ (fat)=1.42; $n_2$ (muscle)=1.296; $k_1=k_2=0.0004$; and n (flint)=1.588. The laser radiation was taken as perpendicularly polarized. The relative reflectance for fat (dashed line) and muscle (solid line) are shown in FIG. 8.

Figure 8:
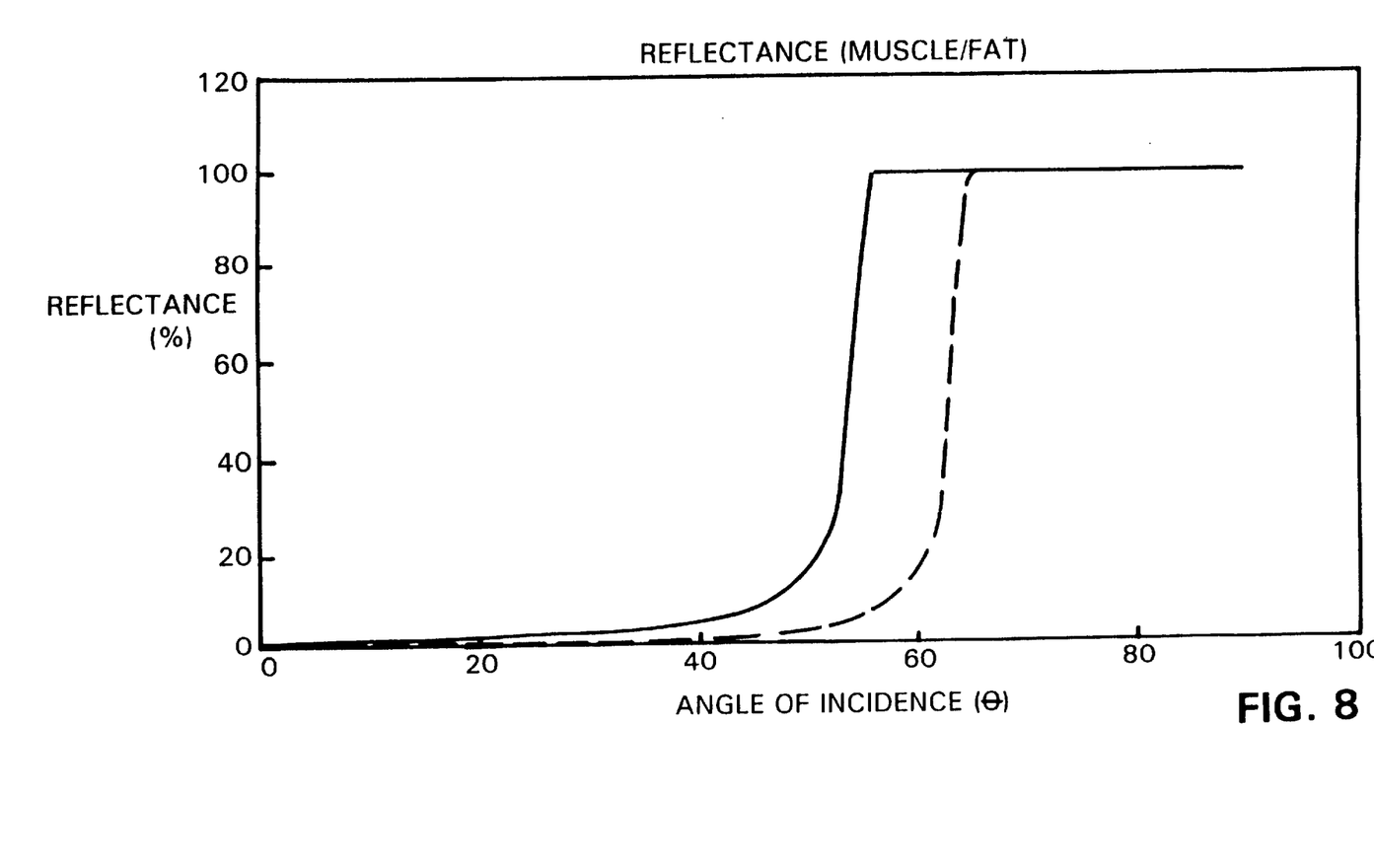

As shown in FIG. 8 there is substantial selectivity for incident angles between about 50° and 60°. In particular, at an incident angle of 56°, the reflectivity from muscle tissue is about 99%, whereas the reflectivity from fat tissue is about 6%. Thus, a probe providing an incident angle of 55° and having a flint glass prism and a 2.13 micron wavelength delivered from a Holmium:YAG laser will be suitable to selectively deliver laser radiation to fat and not muscle.

OTHER EMBODIMENTS

It is to be understood that while the invention has been described in conjunction with the detailed description thereof, that the foregoing description is intended to illustrate and not limit the scope of the invention, which is defined by the scope of the appended claims. For example, in other embodiments, the probe can selectively deliver laser radiation to a first non-biological substrate having a first index of refraction and not to a second non-biological substrate having a second index of refraction less than the first index. The non-biological substrates can be, e.g., the surfaces of metals, ceramics, plastics, semiconductors, or other solid materials.

Other aspects, advantages, and modifications are within the scope of the following claims.

What is claimed is:

1. A probe for selectively delivering laser radiation to a first tissue, having a first index of refraction relative to a second tissue having a second index of refraction less than the first index, the probe comprising:
   a laser transmitting medium comprising an optical axis and a tissue-contacting surface, the optical axis contacting the tissue-contacting surface at an angle that is less than the critical angle for an interface between the tissue-contacting surface and the first tissue and greater than or equal to the critical angle for an interface between the tissue-contacting surface and the second tissue, wherein during operation the probe directs the laser radiation along the optical axis to the tissue-contacting surface.

2. The probe of claim 1, wherein the angle is substantially equal to a principle angle for optimal transmission when the tissue-contacting surface contacts the first tissue.

3. The probe of claim 1, wherein the first tissue consists essentially of fat.

4. The probe of claim 1, wherein the second tissue consists essentially of muscle.

5. The probe of claim 1, wherein the first index of refraction is greater than 1.4 at the wavelength of the laser radiation.

6. An apparatus comprising the probe of claim 1 and a laser radiation source coupled to the probe for delivering the laser radiation to the probe.

7. The apparatus of claim 6, wherein the laser radiation source comprises a diode laser, Nd:YAG laser, CTE:YAG laser, ErCr:YSGG laser, holmium laser, erbium laser, $CO_2$ laser, or dye laser.

8. The apparatus of claim 6, wherein the first tissue consists essentially of fat and the second tissue consists essentially of muscle.

9. The probe of claim 1, further comprising an optical fiber defining the optical axis, wherein during operation the fiber directs the laser radiation to the tissue-contacting surface.

10. The probe of claim 9, further comprising a prism connected to an end of the optical fiber, wherein during operation the fiber directs the laser radiation into the prism through a first face of the prism and towards a second face of the prism, the second face of the prism forming the tissue-contacting surface.

11. The probe of claim 10, wherein during operation the laser radiation reflected from the second face of the prism propagates along a path within the prism that is substantially normal to a third face of the prism.

12. The probe of claim 11, wherein the third face of the prism has a reflective coating.

13. The probe of claim 11, wherein the first tissue consists essentially of fat and the second tissue consists essentially of muscle.

14. The probe of claim 10, further comprising a second fiber, wherein during operation the second and one or more additional faces of the prism direct laser radiation reflected from the second face to the second fiber, which carries the reflected radiation away from the prism.

15. The probe of claim 14, wherein the first tissue consists essentially of fat and the second tissue consists essentially of muscle.

16. The probe of claim 1, wherein the second tissue consists essentially of blood vessels.

17. The probe of claim 1, wherein the second tissue consists essentially of skin.

18. The probe of claim 1, wherein the first tissue consists essentially of fat and the second tissue consists essentially of muscle.

19. A method for selectively delivering laser radiation to a first tissue in a patient relative to an adjacent second tissue in a patient, the first tissue having a first index of refraction and the second tissue having a second index of refraction that is less than the first index of refraction, the method comprising:
   contacting the first tissue in the patient with a probe; and
   delivering the laser radiation to the patient through the probe at a first angle of incidence greater than the critical angle for an interface between the probe and the second tissue.

20. The method of claim 19, further comprising:
   redirecting laser radiation reflected from the first tissue or second tissue in the patient back to the tissue at a second angle of incidence substantially equal to the first angle of incidence.

21. The method of claim 19, further comprising:
   directing laser radiation reflected from the first tissue or second tissue in the patient away from the patient.

22. The method of claim 19, wherein the first angle is substantially equal to a principle angle for optimal transmission when the probe contacts the first tissue.

23. The method of claim 19, wherein the first tissue consists essentially of fat.

24. The method of claim 19, wherein the second tissue consists essentially of muscle.

25. The method of claim 19, wherein the first tissue consists essentially of fat and the second tissue consists essentially of muscle.

26. The method of claim 19, wherein the first index of refraction is greater than 1.4 at the wavelength of the laser radiation.

27. The method of claim 19, wherein the laser radiation is derived from a diode laser, Nd:YAG laser, CTE:YAG laser, ErCr:YSGG laser, holmium laser, erbium laser, $CO_2$ laser, or dye laser.

28. A probe for selectively delivering laser radiation to a first tissue having a first index of refraction relative to an adjacent second tissue having a second index of refraction less than the first index, the probe comprising:
   a laser transmitting medium comprising an optical axis and a tissue-contacting surface, the optical axis forming an angle with the tissue-contacting surface, wherein during operation the probe directs the laser radiation along the optical axis to the tissue-contacting surface, transmits a first amount of laser energy through the tissue-contacting surface when contacting the first tissue, and transmits a second amount of laser energy through the tissue-contacting surface when contacting the second tissue, and wherein the angle is selected such that the first amount of laser energy is at least twice the second amount of laser energy.

29. The probe of claim 28, wherein the angle is selected such that the first amount of laser energy is at least four times the second amount of laser energy.

30. The probe of claim 28, wherein the angle is substantially equal to a principle angle for optimal transmission when the tissue-contacting surface contacts the first tissue.

31. The probe of claim 28, wherein the first tissue consists essentially of fat.

32. The probe of claim 28, wherein the second tissue consists essentially of muscle.

33. The probe of claim 28, wherein the first index of refraction is greater than 1.4 at the wavelength of the laser radiation.

34. The probe of claim 28, further comprising an optical fiber defining the optical axis, wherein during operation the fiber directs the laser radiation to the tissue-contacting surface.

35. The probe of claim 34, further comprising a prism connected to an end of the optical fiber, wherein during operation the fiber directs the laser radiation into the prism through a first face of the prism and towards a second face of the prism, the second face of the prism forming the tissue-contacting surface.

36. The probe of claim 35, further comprising a second fiber, wherein during operation the second and one or more additional faces of the prism direct laser radiation reflected from the second face to the second fiber, which carries the reflected radiation away from the prism.

37. The probe of claim 35, wherein during operation the laser radiation reflected from the second face of the prism propagates along a path within the prism that is substantially normal to a third face of the prism.

38. The probe of claim 37, wherein the third face of the prism has a reflective coating.

39. The probe of claim 28, wherein the second tissue consists essentially of blood vessels.

40. The probe of claim 28, wherein the second tissue consists essentially of skin.

41. The probe of claim 28, wherein the first tissue consists essentially of fat and the second tissue consists essentially of muscle.

42. An apparatus comprising the probe of claim 18 and a laser radiation source coupled to the probe for delivering the laser radiation to the probe.

43. The apparatus of claim 42, wherein the laser radiation source comprises a diode laser, Nd:YAG laser, CTE:YAG laser, ErCr:YSGG laser, holmium laser, erbium laser, $CO_2$ laser, or dye laser.

44. The apparatus of claim 42, wherein the first tissue consists essentially of fat and the second tissue consists essentially of muscle.

45. A method for selectively delivering laser radiation to a first tissue of a patient relative to an adjacent second tissue in the patient, the first tissue having a first index of refraction and the second tissue having a second index of refraction that is less than the first index of refraction, the method comprising:

contacting the patient with a probe; and delivering the laser radiation to the patient through the probe at an angle of incidence such that the energy transmitted into the first tissue when the probe contacts the first tissue is at least twice the energy transmitted into the second tissue when the probe contacts the second tissue.

46. The method of claim 45, wherein the angle of incidence is such that the energy transmitted into the first tissue when the probe contacts the first tissue is at least four times the energy transmitted into the second tissue when the probe contacts the second tissue.

47. The method of claim 45, wherein the first angle is substantially equal to a principle angle for optimal transmission when the probe contacts the first tissue.

48. The method of claim 45, wherein the first tissue consists essentially of fat.

49. The method of claim 45, wherein the second tissue consists essentially of muscle.

50. The method of claim 45, wherein the first tissue consists essentially of fat and the second tissue consists essentially of muscle.

51. The method of claim 45, wherein the first index of refraction is greater than 1.4 at the wavelength of the laser radiation.

52. The method of claim 45, wherein the laser radiation is derived from a diode laser, Nd:YAG laser, CTE:YAG laser, ErCr:YSGG laser, holmium laser, erbium laser, $CO_2$ laser, or dye laser.

* * * * *